United States Patent [19]

Daum et al.

[11] Patent Number: 4,959,484

[45] Date of Patent: Sep. 25, 1990

[54] NOVEL STROBILURINE DERIVATIVES, THEIR PREPARATION AND THEIR USE

[75] Inventors: Lothar Daum, Otterstadt; Gerhard Keilhauer, Dannstadt-Schauernheim; Gisela Lorenz, Neustadt; Eberhard Ammermann, Ludwigshafen; Wolfgang Weber, both of Kaiserslautern; Wolfgang Steglich, Bonn-Roettgen; Bert Steffan, Rheinbach; Angela Scherer, Bonn, all of Fed. Rep. of Germany

[73] Assignee: BASF Aktiengesellschaft, Ludwigshafen, Fed. Rep. of Germany

[21] Appl. No.: 338,174

[22] Filed: Apr. 14, 1989

[30] Foreign Application Priority Data

May 6, 1988 [DE] Fed. Rep. of Germany ....... 3815484

[51] Int. Cl.$^5$ .......................................... C07D 319/20
[52] U.S. Cl. ..................................................... 549/334
[58] Field of Search ........................................ 549/334

[56] References Cited

PUBLICATIONS

The Journal of Antibiotics, 32 (1979), pp. 1113–1117.
The Journal of Antibiotics, 36 (1983), pp. 661–666.
"Cellular Regulation and Malignant Growth", Springer-Verlag, Berlin, 1985, pp. 169–176.

*Primary Examiner*—Nicky Chan
*Attorney, Agent, or Firm*—Oblon, Spivak, McClelland, Maier & Neustadt

[57] ABSTRACT

Novel strobilurine derivatives which are suitable for the treatment of disorders and as fungicides are described.

1 Claim, No Drawings

NOVEL STROBILURINE DERIVATIVES, THEIR PREPARATION AND THEIR USE

The present invention relates to novel strobilurine derivatives, processes for their preparation and their use for the treatment of diseases and for controlling phytopathogenic fungi.

The Journal of Antibiotics 32 (1979), 1113-1117, ibid. 36 (1983), 661-666, and Cellular Regulation and Malignant Growth, Springer-Verlag, Berlin 1985, pages 169-176, describe the compounds strobilurine and oudemansine and their derivatives. These compounds have a strong antifungal and cytostatic activity.

Strobilurines A, B and C and oudemansines A and B were isolated from the genera Strobilurus, Oudemansiella, Xerula, Cyphellopsis, Hydropus and Mycena. All compounds inhibit the respiration of eucaryotes and hence the growth of fungi and cells. The strobilurines and oudemansines bind reversibly to the $b_t$ center of cytochrome b in complex III of the mitochondrial respiratory chain.

We have found that strobilurine derivatives of the formula I

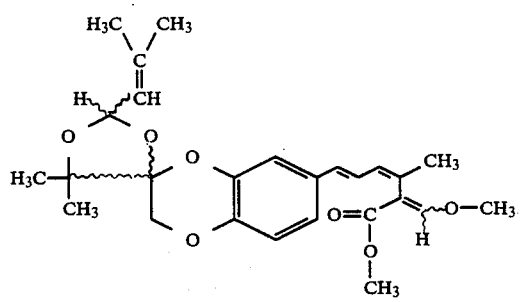

have a better action.

The novel compounds can be prepared by cultivating a microorganism which forms the strobilurine derivatives of the formula I and is of the genus Crepidotus, and isolating the strobilurine derivatives of the formula I from the mycelium.

Microorganisms of the genus Crepidotus are available from the known repositories. Using a simple small-scale test, it is possible to select from these microorganisms those which form the novel compounds. One such microorganism is the strain DSM 4545, which is obtainable from the Deutsche Sammlung für Mikroorganismen in Braunschweig.

Suitable nutrient media for the cultivation of microorganisms are the conventional ones which contain carbon sources, nitrogen sources, inorganic salts and, if required, small amounts of trace elements and vitamins. Suitable nitrogen sources are inorganic or organic nitrogen compounds or materials which contain these compounds. Examples are ammonium salts, corn steep liquor, brewer's yeast autolysate, soybean meal hydrolysate, wheat gluten, yeast extract, yeast, urea and potato protein. The use of corn steep liquor is particularly advantageous. Suitable carbon sources are sugars, such as D-glucose, mannose or galactose, polyalcohols, such as mannitol, and alcohols, such as ethanol.

Examples of inorganic salts are the salts of calcium, magnesium, manganese, potassium, zinc, copper, iron and other metals. A particular example of an anion of the salts is the phosphate ion. If necessary, growth factors, for example pantothenic acid, p-aminobenzoic acid and thiamine, are added to the nutrient medium. The mixing ratio of the stated nutrients depends on the type of fermentation and is determined from case to case.

The novel compounds are isolated from the mycelium after the fermentation. For this purpose, the mycelium is separated off from the culture broth and dried. The mycelium is extracted with a polar solvent, such as a low molecular weight alcohol, the novel compounds going into solution. The extract thus obtained is evaporated down and the residue is purified by chromatography.

The novel compounds, in particular the substance of Example 1, have a good antiviral, antiproliferative and cytotoxic activity. They also have a good antifungal action.

They are furthermore distinguished by good activity against a broad spectrum of phytopathogenic fungi, in particular from the class consisting of the Ascomycetes and Basidiomycetes. Some of them have systemic activity and can be used as foliage fungicides and soil fungicides.

They can therefore be employed for the treatment of solid tumors, such as carcinomas of the breast, lung, colon and kidney, of acute and chronic leukemia and of viral diseases, such as herpes infections.

The novel compounds are particularly important for controlling a large number of fungi in various crops or their seeds, in particular wheat, rye, barley, oats, rice, corn, lawns, cotton, soybean, coffee, sugar cane, fruit and ornamentals in horticulture, in viticulture and in vegetables, such as cucumbers, beans and cucurbitaceae.

The novel compounds are particularly suitable for controlling the following plant diseases:
*Erysiphe graminis* (powdery mildew) in cereals,
*Erysiphe cichoracearum* and *Sphaerotheca fuliginea* on cucurbitaceae,
*Uncinula necator* on grapevines,
*Puccinia* species on cereals,
*Rhizoctonia* species on cotton and lawns,
*Venturia inaequalis* (scab) on apples,
Helminthosporium species on cereals,
*Septoria nodorum* on wheat,
*Botrytis cinerea* (gray mold) on strawberries and grapevines,
*Cercospora arachidicola* on peanuts,
*Pseudocercosporella herpotrichoides* on wheat and barley,
*Fusarium* and *Verticillium* species on various plants,
*Plasmopara viticola* on grapevines and
*Alternaria* species on vegetables and fruit.

The compounds are used by spraying or dusting the plants with the active ingredients or treating the seeds of the plants with the active ingredients. They are applied before or after infection of the plants or seeds with the fungi.

EXAMPLE 1

200 ml of a preculture medium which contained 20 g/l of glucose, 5 g/l of peptone, 5 g/l of yeast extract, 0.5 g/l of $KH_2PO_4$, 1 g/l of $MgSO_4 \cdot 7H_2O$, 10 mg/l of $FeCl_3$, 1.78 mg/l of $ZnSO_4$ and 73.5 mg/l of $CaCl_2$ were introduced into a 500 ml conical flask having a side arm. The medium was inoculated with agar pieces grown through with mycelia of a Crepidotus culture (DSM 4545) and incubated for 14 days at room temperature at 120 rpm. Thereafter, the content was transferred to a 25

1 fermenter which contained 20 l of the same medium. The pH of the medium was 5.8. The culture was then incubated for 21 days at room temperature while stirring at 200 rpm and aerating at a rate of 2 /min.

20 l of the culture broth were then filtered, and the mycelium cake obtained was freeze-dried. The lyophilisate (271 g) was extracted with 10 l of methanol. The methanolic mycelium suspension was filtered and the filtrate was evaporated down under reduced pressure at 45° C. The oily extract obtained (98 g) was adsorbed onto silica gel. This was introduced onto a column (80 cm×5 cm) containing 200 g of silica gel and equilibrated with toluene.

The column was eluted with toluene/ethyl acetate (volume ratio 90:10), and, after the first 200 ml, a 500 ml fraction obtained was evaporated down and the residue was rechromatographed over an RP18 silica gel column (23 cm×2.5 cm). Elution was carried out using 8 : 2 methanol/water. After the first 420 ml, 100 ml of a fraction which contained 96 mg of a pure compound were obtained.

This compound had the following physical and chemical properties:

(1) Appearance: colorless oil
(2) Empirical formula: $C_{26}H_{32}O_7$
(3) Molecular weight: 456
(4) UV absorption spectrum:
Absorption maxima at

| Absorption maxima at |
| --- |
| 230 nm ($\epsilon$ = 7692) |
| 300 nm ($\epsilon$ = 6730) |
| 320 nm ($\epsilon$ = 6730) |

(5) IR absorption spectrum [$cm^{-1}$] (KBr disk): 3450(st), 2980(st), 1710(sst), 1530(st), 1510(sst), 1435(st), 1390(w), 1290(sst), 1210(sst), 1150/1120(sst), 1040(sst), 970(st), 910(st), 810(st), 775(st).

(6) NMR spectrum $^1$H- and $^{13}$C-NMR data, $\delta$ values (400 MHz or 100.62 MHz, MeOD as internal standard)

| | | | | |
| --- | --- | --- | --- | --- |
| 1-H | 6.93 | 1.5 | C-1 | 115.67 |
| | | | C-2 | 142.86 |
| | | | C-3 | 143.46 |
| 4-H | 6.82 d | 8 | C-4 | 117.74 |
| 5-H | 6.91 dd | 8/1.5 | C-5 | 121.33 |
| | | | C-6 | 133.56 |
| 7-H | 6.39 d | 16 | C-7 | 131.24 |
| 8-H | 6.47 dd | 16/10.5 | C-8 | 126.68 |
| 9-H | 6.19 d | 10.5 | C-9 | 130.99 |
| | | | C-10 | 131.67 |
| | | | C-11 | 111.60 |
| 12-H | 7.53 s | | C-12 | 160.52 |
| 14-CH | 1.93 s | | C-14 | 23.81 |
| 15-CH | 3.85 s | | C-15 | 62.32 |
| 16-CH | 3.73 s | | C-16 | 51.96 |
| 1'-H | 4.27 d | 10.5 | C-1' | 66.88 |
| 1'-H | 4.07 d | 10.5 | | |
| | | | C-2' | 102.56 |
| | | | C-3' | 84.10 |
| 4'-CH | 1.42 s | | C-4' | 22.05 |
| 5'-CH | 1.32 s | | C-5' | 25.14 |
| 6'-H | 5.97 d | 7.5 | C-6' | 99.6 |
| 7'-H | 5.23 d | 7.5 | C-7' | 123.14 |
| | | | C-8' | 142.46 |
| 9'-CH | 1.73 s | | C-9' | 18.31 |
| 10'-CH | 1.78 s | | C-10' | 25.93 |

(7) Solubility: Slightly soluble in ethyl acetate, acetone, methanol and ethanol. Hardly soluble in water.

(8) Thin layer chromatography on silica gel (silica gel 60 $F_{254}$ E. Merck); development with toluene/ethyl acetate (volume ratio 90 : 10): $R_f$=0.47

(9) MS (DE 180° C.): 456.21 (100, M, calculated for $C_{26}H_{32}O_7$, 456.27), 425(4), 372(10), 319(10) , 313(10), 297(5), 256(14), (90), 207(14), 167(38), 153(10), 141(8), 115(8), 83(20), 75(58), 55(20), 41 (22).

According to the structural analysis, the compound has the following formula:

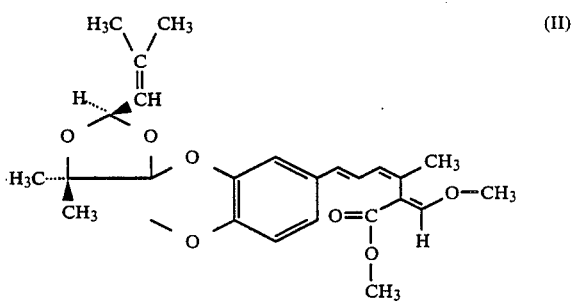

EXAMPLE 2

Respiration-inhibiting action with Penicillium notatum

The oxygen consumption was measured by polarography in an air-tight vessel having a volume of 3 ml and equipped with a magnetic stirrer and an oxygen electrode. The test fungus was grown from a spore suspension to a mycelium weight of 10–20 mg/ml of medium. The measurements were carried out at a mycelium concentration of 25–30 mg moist mycelium weight per ml in 1% strength glucose solution. After constant respiration for a short time, the compounds dissolved in methanol were added to the suspension and the $O_2$ consumption was recorded.

The experiment was carried out using the compound of Example 1 and strobilurine A and oudemansine A as comparative compounds. The results of the percentage inhibition of respiration are stated in Table 1.

TABLE 1

| Inhibition of respiration as a percentage of the control | | |
| --- | --- | --- |
| | ($\mu$g/ml) | |
| Test compounds | 0.4 | 0.04 |
| Substance of Example 1 | 95 | 93 |
| Strobilurine A | 94 | 65 |
| Oudemansine A | 93 | — |

EXAMPLE 3

Action on the incorporation of radioactive intermediates into cells of HeLa-S3 and ECA $^{14}$C-uridine was used as an intermediate for RNA biosynthesis, $^{14}$C-thymidine was used as an intermediate for DNA biosynthesis and $^{14}$C-leucine was used as an intermediate for protein biosynthesis.

HeLa-S3 or ECA cells in a concentration of from $5.10^5$ to $1.10^6$ cells/ml in PBS, with or without glucose (0.01% w/v), were added to the substance of Example 1. The cells were preincubated at 37° C. on a shaking machine for 20 minutes with the substance of Example 1. 1 ml of the suspension was added to each of the intermediates (0.1 $\mu$Ci) and incubation was carried out again for 30 minutes at 37° C. The incorporation of radioactive intermediates was stopped by subsequent addition of 1 ml of ice-cold TCA (10%). The acid-insoluble precipitate was collected on a cellulose nitrate filter and washed with 5 ml of ice-cold TCA (5%). After drying, the filters were covered with a layer of 5 ml of scintillation liquid and the radioactivity was determined in a liquid scintillation counter.

The results are expressed as a percentage of the total incorporation, for HeLa-S3 in Table 2 and for ECA in Table 3.

TABLE 2

| Intermediates | Incorporation as a percentage of the controls (=100%) Test solution (µg/ml) | | |
|---|---|---|---|
| | 25 | 5 | 1 |
| Uridine + glucose | 97 | 90 | 93 |
| Uridine | 64 | 60 | 64 |
| Thymidine + glucose | 96 | 98 | 100 |
| Thymidine | 91 | 91 | 99 |
| Leucine + glucose | 90 | 85 | 94 |
| Leucine | 90 | 88 | 89 |

TABLE 3

| Intermediates | Incorporation as a percentage of the controls (= 100%) Test solution (µg/ml) | | |
|---|---|---|---|
| | 25 | 5 | 1 |
| Uridine + glucose | 88 | 90 | 80 |
| Uridine | 10 | 11 | 7 |
| Thymidine + glucose | 96 | 98 | 92 |
| Thymidine | 3 | 2 | 2 |
| Leucine + glucose | 83 | 77 | 81 |
| Leucine | 2 | 2 | 2 |

EXAMPLE 4

Cytostatic action on HeLa-S3 cells

Incubation of HeLa-S3 and other cells with the novel compound inhibits cell division within a short time. In the case of HeLa-S3 cells, the compound is nontoxic in relatively high concentrations (25 µg/ml). Inhibition at low concentrations (0.025–0.25 µg/ml) can be reversed by replenishing the medium. The cell density was measured by determining the total protein content per well.

The experiment was carried out using the compound of Example 1, and strobilurine A and oudemansine A as comparative compounds. The values mentioned indicate the results after incubation for 3 days with the test substances and are expressed in Table 4 as a percentage of the total protein in the untreated control.

TABLE 4

| Test compound | Protein content as a percentage of the control (µg/ml) | | |
|---|---|---|---|
| | 2.5 | 0.25 | 0.025 |
| Substance of Example 1 | 20 | 32 | 32 |
| Strobilurine A | 21 | 47 | 79 |
| Oudemansine A | 47 | 59 | 77 |

EXAMPLE 5

Cytotoxic and antiproliferative action on human tumor cells

To determine the antitumor properties of the substance of Example 1, human tumor cells from different tissues (5637-6: carcinoma of the bladder; HT-29: carcinoma of the colon; MCF-7: carcinoma of the breast) were used.

From 1 to $2 \cdot 10^3$ tumor cells in a state of exponential growth were plated out in 96-well plates in complete growth medium (RPMI 1640 + 10% fetal calf's serum) and incubated overnight under standard culture conditions (37° C., 5% carbon dioxide, water vapor-saturated atmosphere). The substance was added the next day, serial titrations of the substance of Example 1 being prepared over a concentration range of from $10^{-4}$ to $10^{-9}$ M After further incubation for 72 h under standard conditions, the cell count was determined by staining with crystal violet and subsequent photometric evaluation at 540 nm with the aid of a multiphotometer.

Only at the very high concentration of $10^{-4}$ M was cytolysis of the treated cells detected under the microscope. At the other concentrations investigated, pronounced, dose-dependent inhibition of cell proliferation was observed, so that even at the lowest investigated concentration of $10^{-9}$ M, the number of treated cells gave a value smaller than 50% of the untreated cell control.

The pronounced decrease in proliferative activity of the cells treated with the substance of Example 1 is accompanied by a morphological change, characterized by an elongation of the cell bodies and by the formation of cell processes.

EXAMPLE 6

Antiviral action on VSV in HEp-2 cells

The determination of the antiviral activity of a test compound is based on the measurement of the protection of human HEp-2 cells as indicator cells from the cytopathic effect (CPE) of Vesicular Stomatitis virus (VSV).

For this purpose, 100 µl of culture medium containing $2 \times 10^4$ HEp-2 cells were introduced into the wells of a 96-well flat-base plate and incubated overnight at 37° C. and under 5% (v/v) of carbon dioxide. The next day, 100µl of the sample solution were added to the confluent cell cultures and serially titrated twice. Furthermore, a cell control (=untreated cells not infected with virus) and a virus control (=untreated cells infected with virus) were run simultaneously on the culture plate. After a further incubation time of 24 h at 37° C and under 5% (v/v) of $CO_2$, the cultures were infected with 50µl of a VSV suspension in culture medium and incubated at 37° C. and under 5% (v/v) of $CO_2$. After 2 days, the virusrelated cell destruction (CPE) in the unprotected cultures (=virus control) was complete. The percentage of protected cells in the cultures treated with the test compound and then infected with VSV was determined by staining with crystal violet. The sample concentration which leads to 50% protection as determined as a measure of antiviral activity, based on zero and 100% protection. Recombinant human γ-interferon (rHuIFN-γ) was simultaneously investigated as a control for the antiviral activity of a compound.

Table 5 shows the test substance with the concentration which provides the HEp-2 cells with 50% protection from the cytopathic effect of VSV.

TABLE 5

| Test compound | Antiviral activity (ng/ml) |
|---|---|
| Substance of Example 1 | 5 |
| Control (rHuIFN-γ) | 0.5 |

In contrast to rHuIFN-γ, the substance of Example 1 also had an antiproliferative action under these test conditions, compared with the cell control. The antiviral and antiproliferative activities of the substance of Example 1 were parallel and were correlated with a morphological change in the cells, i.e. the cells were elongated compared with the cell control and had neurite-like processes.

When the substance of Example 1 or rHuIFN-γ was sucked off from the cell culture prior to the addition of VSV, the cells were still protected from the CPE of VSV, although to a lesser extent. This shows that, as described for the interferons, the substance of Example 1 does not react directly with the viruses but converts the cells into a state in which no virus multiplication can take place in them.

EXAMPLE 7

Antiviral action on VSV in BHK-21 cells

A 96-well microtiter plate was inoculated with BHK-21 cells ($1.10^4$ to $5.10^4$ cells/ml) and incubated for 24 hours with G-MEM medium (10% of serum). After this time, the medium was sucked off and the cells were infected with 25 μl of VSV suspension (250 PFU/well). After 1 h, 75μl of medium containing the test compounds (G-MEM containing 2% of serum) were added to the test batches. In the course of the test duration of 24 h, 10 μl of the cell supernatants were sucked off 3 times and the virus titer was determined from these.

For the titer determination, BHK-21 cells were grown on 6-well test plates, the 10 μl samples were appropriately diluted and the cells were infected with these solutions. After 1 h, the solutions were sucked off and the cells were covered with a layer of an agar medium (1% (w/v) of agar, MEM medium without phenol red). After 24 h, the cells were stained with neutral red (0.001% w/v) and the plaques were counted.

Table 6 shows the test compounds with the concentrations used and the PFU*/well at the time of sampling.
*PFU=plaque forming unit

TABLE 6

| Test compound | after 14.5 h | PFU/well after 18.5 h | after 23.5 h |
|---|---|---|---|
| Substance of Example 1 (5 μg/ml) | $3.0 \times 10^2$ | $1.0 \times 10^3$ | $1.1 \times 10^4$ |
| Strobilurine A (5 μg/ml) | $1.8 \times 10^2$ | $8.0 \times 10^2$ | $2.1 \times 10^3$ |
| Oudemansine A (50 μg/ml) | $2.8 \times 10^2$ | $1.0 \times 10^3$ | $9.0 \times 10^3$ |
| Control | $6.1 \times 10^4$ | $3.8 \times 10^5$ | $1.0 \times 10^6$ |

EXAMPLE 8

Action on the morphology of HeLa-S3 cells and the adsorption of plant lecithin

HeLa-S3 cells were applied to a 96-well titer plate in a cell density of from $5.10^5$ to $1.10^6$ cells/ml in medium F12. After 24 h, the cells had spread over the surface, and the medium was changed. The cells were incubated twice for 72 h with the medium containing the test compounds. After 72 h, the cells, which normally exhibit epithelium-like growth, possessed a fibroblast-like morphology. The medium was then replaced by the same medium without the test substance.

After 144 h, the medium was sucked off, the cells were washed with PBS and a lecithin obtained from Vicia villosa (specific binding to N-acetyl-D-galactosamine), coupled to a peroxidase and dissolved in serum-free F-12 medium (75 μg/ml), was added. After 60 min, the medium was sucked off, the cells were washed and the peroxidase substrate reaction buffer ($H_2O_2$-ABTS ) was added. After 15 min, the reaction was stopped by adding $NaN_3$; and the absorption of the oxidized ABTS was measured at 405 nm using an 8-channel photometer.
ABTS=2,2'-azino-di-[3-ethylbenzothiazoline sulfonate]

The experiment was carried out using the compound of Example 1, and strobilurine A and oudemansine A as comparative compounds. The results are shown in Table 7, as a percentage of the total activity of unconverted substrate of the untreated control.

TABLE 7

| | Lecithin binding as a percentage of the untreated controls (μg/ml) | | |
|---|---|---|---|
| Test compound | 25 | 10 | 2.5 |
| Subtance of Example 1 | —* | — | 44 |
| Strobilurine A | — | 67 | — |
| Oudemansine A | 67 | — | — |

*— means not tested

EXAMPLE 9

Antifungal action in the plate diffusion test

A medium containing 1.5% (w/v) of agar was poured as a single layer onto test plates containing fungi, mycelium or spore suspension being added shortly before the medium had become cold. Filter rondelles (6 mm diameter) were impregnated with antibiotic-containing solution (10 μl) and placed on the test plate. The inhibitory areolas were measured after an incubation time of 24 h at 27° C. The results are stated in Table 8. The concentration of the test solutions was 5 μg/rondelle.

TABLE 8

| Test organisms | Diameter of inhibitory areola (mm) |
|---|---|
| Alternaria porri | 20i * |
| Cladosporium cladosporoides | 20i |
| Currularia lunata | 17i |
| Mucor miehei | 20 |
| Nematospora coryli | 23i |
| Neurospora crassa | 25i |
| Penicillium notatum | 15i |

*i = incomplete inhibitory areola

EXAMPLE 10

Activity against wheat brown rust

Leaves of wheat seedlings of the variety "Frühgold" which had been grown in pots were dusted with spores of brown rust (Puccinia recondita). The pots were then placed for 24 h at from 20° to 22° C. in a chamber with a high atmospheric humidity (from 90 to 95%). During this time, the spores germinated and the germ tubes penetrated the leaf tissue. The infected plants were then sprayed dripping wet with aqueous spray liquors which contained 80% of active ingredient and 20% of emulsifier in the dry substance. After the spray coating had dried on, the test plants were placed in a greenhouse at from 20° to 22° C. and from 65 to 70% relative humidity. After 8 days, the extent of development of rust fungi on the leaves was determined.

|  | Infestation of the leaves after application of 0.025% strength aqueous active ingredient |
|---|---|
| Action | formulation |
| Example 1 | |
| Substance of | 2 |
| Tridemorph | 4 |
| Untreated | 5 |
Rating: 0 = no fungal infestation, in stages to 5 = total infestation
The comparative substance tridemorph (=N-tridecyl-2,6-dimethylmorpholine) is disclosed as a fungicide in DE 1 164 152.
We claim:
1. A compound of the formula
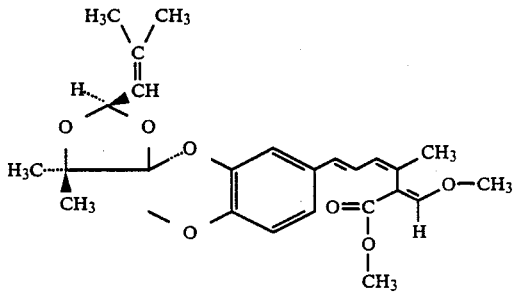
(II)
* * * * *